United States Patent [19]

Kordes

[11] Plant 4,421

[45] May 29, 1979

[54] ROSE PLANT

[75] Inventor: Reimer Kordes, Sparrieshoop, Fed. Rep. of Germany

[73] Assignee: Jackson & Perkins Co., Medford, Oreg.

[21] Appl. No.: 918,559

[22] Filed: Jun. 23, 1978

[51] Int. Cl.[2] ..... A01H 5/00

[52] U.S. Cl. ..... Plt./24

[58] Field of Search ..... Plt./24

*Primary Examiner*—Robert E. Bagwill

*Attorney, Agent, or Firm*—Klarquist, Sparkman, Campbell, Leigh, Hall & Whinston

[57] ABSTRACT

A vigorous rose plant of the floribunda class, characterized particularly by its pointed flower bud and petal formation, its high resistance to rose powdery mildew, with continuous flowering blooms with little or no fragrance.

1 Drawing Figure

BACKGROUND OF THE INVENTION

The present invention relates to a new and distinct variety of rose plant of the floribunda class which was originated by me by crossing the variety Berolina with pollen of an unnamed seedling variety.

The primary objective of this breeding was to produce a new and improved variety of the floribunda class, bearing yellow buds on stems suitable for cutting and with other growth characteristics desirable in a greenhouse cut-flower variety.

This objective was fully achieved along with other desirable improvements as evidenced by the following unique combination of characteristics which are outstanding in the new variety and which distinguish it from its parents as well as from all other varieties of which I am aware:

1. A vigorous plant.
2. Foliage which is very resistant to rose powdery mildew.
3. Continuous blooming in a greenhouse environment, producing very few non-flowering, "blind", shoots.
4. Pointed bud form.
5. Bud color of Maize Yellow opening to a flower color of Indian Yellow.
6. Very little or no fragrance.
7. Petals which roll back making each one appear slightly quilled.

Asexual reproduction of this new variety by budding as performed at Sparrieshoop, West Germany, and at Irvine, Calif., shows that the aforementioned characteristics come true to form and are established and transmitted through succeeding propagations.

The accompanying illustration shows typical specimens of the vegetative growth and flowers of this new variety in different stages of development and as depicted in color as nearly true as it is reasonably possible to make the same in a color illustration of this character.

The following is a detailed description of my new rose cultivar with color in terminology in accordance with Wilson's Horticultural Color Chart except where ordinary dictionary significance of color is indicated.

Parentage:

*Seed parent.*—Berolina.

*Pollen parent.*—Unnamed seedling variety.

Classification:

*Botanical.*—Rosa hybrid.

*Commercial.*—Floribunda.

FLOWER

Observations made from specimens grown at Irvine, Calif., in April, 1978 of greenhouse plants.

Blooming habit: Continuous.

Bud:

*Size.*—1¼ inches when petals start to unfurl.

*Form.*—Pointed, broad base.

*Color.*—When sepals first divide, Maize Yellow (607); when half blown, upper side of petals Indian Yellow (6), with a zone, approximately ¼ petal area, near base of a lighter yellow, Lemon Yellow (4); lower side of petals near Indian Yellow (6/1).

*Sepals.*—Color: Outer surface Scheeles Green (860/3); inner surface Scheeles Green (860/3) with a very light or small amount of tomentum; three appendaged sepals lightly appendaged.

*Receptacle.*—Color: Scheeles Green (860/3). Shape: Funnel. Size: Large, long. Surface: Smooth.

*Peduncle.*—Length: Medium. Surface: Glandular. Color: Light green. Strength: Stiff, erect.

*Opening.*—Petals curl, leaving the center pointed.

Bloom:

*Size.*—Medium. Average open size 3".

*Borne.*—Singly, in irregular clusters.

*Stems.*—Long to medium, strong.

*Form.*—When first open, center petals usually balled. Permanence: Flattens, all petals curl.

*Petalage.*—Number of petals under normal conditions: 20–30.

*Color.*—Center of flower: Upper side of petals Indian Yellow (6). Reverse side of petals Indian Yellow (6/1). Base of petals Indian Yellow (6). General tonality from a distance Indian Yellow.

*Variegations.*—None.

*Discoloration.*—General tonality at end of first day, Indian Yellow (6); third day, Indian Yellow (6/2).

*Fragrance.*—None.

Petals:

*Texture.*—Thick.

*Shape.*—Oval.

*Form.*—Edges slightly quilled.

*Arrangement.*—Imbricated. Petaloids in center, few.

*Persistence.*—Drop off cleanly.

*Lastingness.*—On the plant, very long. As cut flower, very long.

Reproductive parts:

*Stamens, anthers.*—Large. Color, yellow. Arrangement, regular around styles.

*Filaments.*—Color: Yellow.

*Pollen.*—Lemon yellow.

*Styles.*—Color: White.

*Stigmas.*—Color: Uranium Green (63).

PLANT

Form: Bush.

Growth: Very vigorous, upright, branching.

Foliage: Number of leaflets on normal mid-stem leaves: 5–7.

*Size.*—Medium.

*Quantity.*—Normal.

*Color.*—New foliage: Green with a light overlay, especially near edges, of Garnette Brown (00918/3).

Leaflets:

*Shape.*—Oval pointed.

*Texture.*—Leathery.

*Edge.*—Serrated.

*Serrations.*—Single, small.

*Petiole.*—Rachis: Color, reddish. Underside, prickles.

*Stipules.*—Long, bearded.

*Disease resistance.*—Resistant to mildew under normal growing conditions at Irvine, Calif.

Wood:

*New wood.*—Color: Light green. Bark: Smooth.

*Old wood.*—Color: Green.

Prickles:

*Quantity.*—On main stalks from base, few. On laterals from stalk, few.

*Form.*—Narrow base, long, hooked slightly downward.

*Color when young.*—Brown.

*Position.*—Irregular.

Small prickles:

*Quantity.*—None. On laterals, none.

I claim:

1. A new, distinct and improved rose plant of the floribunda class, substantially as illustrated and described, and characterized particularly by its pointed flower bud of Maize Yellow, open flower color of Indian Yellow, its pointed or quilled, petal formation, its heavy petal substance, mildew resistant foliage, continuous flowering without non-blooming shoots and its vigorous plant.

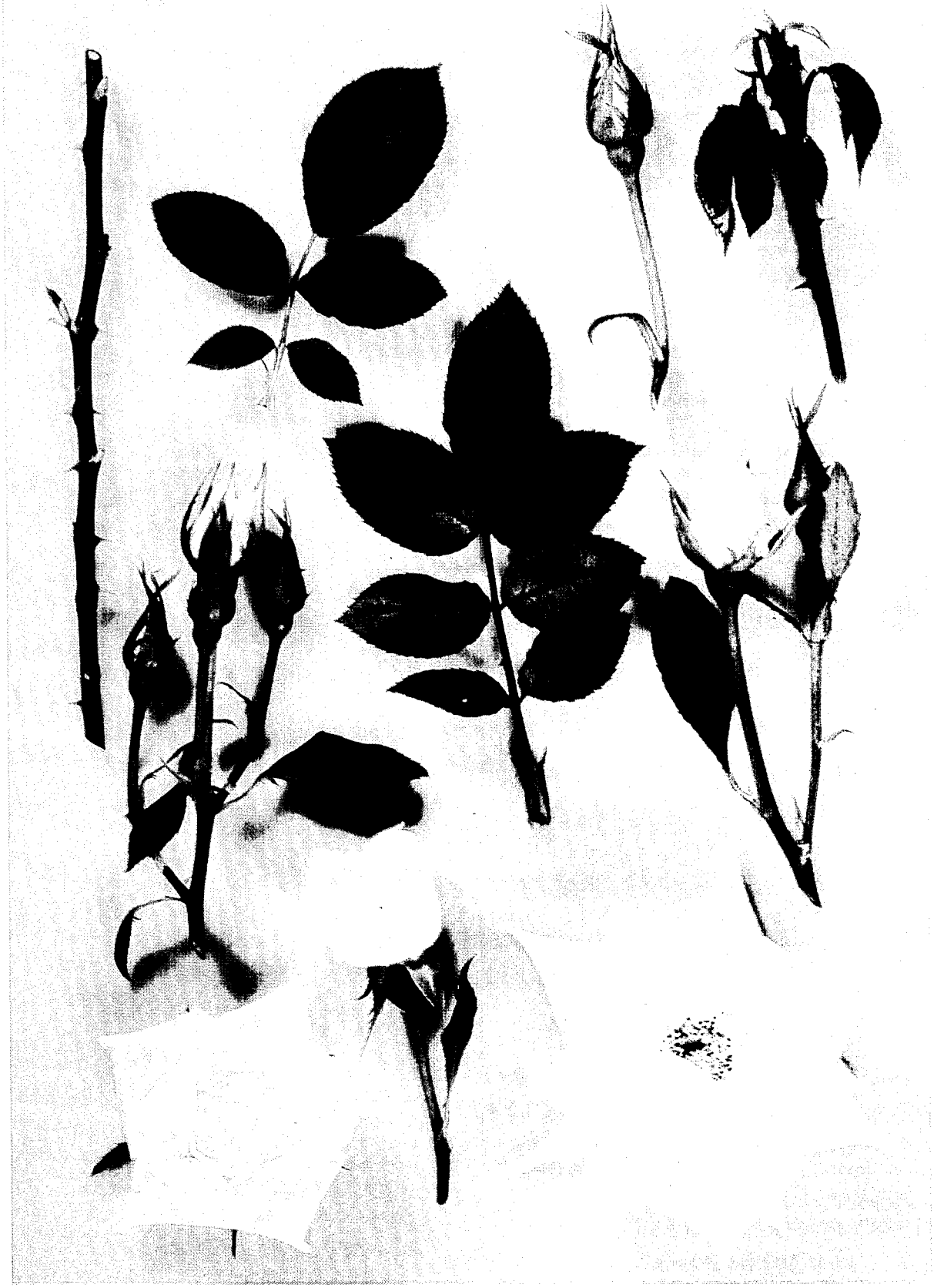

* * * * *